United States Patent [19]

Koike et al.

[11] Patent Number: 4,615,217

[45] Date of Patent: Oct. 7, 1986

[54] TWO-PROBE ULTRASONIC FLAW DETECTION APPARATUS

[75] Inventors: Masahiro Koike, Hitachi; Fuminobu Takahashi, Katsuta; Satoshi Ogura; Kazunori Koga, both of Hitachi, all of Japan

[73] Assignee: Hitachi, Ltd., Tokyo, Japan

[21] Appl. No.: 709,704

[22] Filed: Mar. 8, 1985

[30] Foreign Application Priority Data

Mar. 12, 1984 [JP] Japan ................... 59-45637

[51] Int. Cl.$^4$ ........................................... G01N 29/04
[52] U.S. Cl. ................................................ 73/624
[58] Field of Search ................. 73/624, 602, 618, 620, 73/627

[56] References Cited

U.S. PATENT DOCUMENTS 3,407,650 10/1968 Dickinson, III ...................... 73/624
3,552,191 1/1971 Heseding ............................... 73/624

FOREIGN PATENT DOCUMENTS 58-26550 6/1983 Japan.

*Primary Examiner*—Stephen A. Kreitman
*Attorney, Agent, or Firm*—Antonelli, Terry & Wands

[57] ABSTRACT

A two-probe ultrasonic flaw detection apparatus, in which an ultrasonic wave is transmitted from a transmission probe into an object being inspected and ultrasonic waves reflected from a reflection surface in the object are received by a reception probe, operates to determine the position at which the combined intensity of ultrasonic waves reflected from each part of the reflection surface form a maximum. The reception probe is then moved to the position of maximum reception intensity. The position of maximum reception intensity is determined using as input parameters the ultrasonic characteristics of the object being inspected and of the transmission and reception probes, and the position of the transmission probe and the angle of incidence of the ultrasonic wave into the object.

9 Claims, 11 Drawing Figures

TWO-PROBE ULTRASONIC FLAW DETECTION APPARATUS

FIELD OF THE INVENTION

The present invention relates to an ultrasonic flaw detection apparatus using two probes, and in particular to a two-probe ultrasonic flaw detection apparatus which is suitable for the non-destructive testing of thick-wall materials including those of a pressure vessel, a turbine rotor disc, etc.

BACKGROUND OF THE INVENTION

A tandem scan system using separate probes for transmission and reception which are placed in different positions is employed for detecting flaws in an object being inspected which has a complicated shape, such as a turbine disc, and an apparatus which is provided with these separate probes for transmission and reception is called a two-probe ultrasonic flaw detection apparatus. In this conventional two-probe flaw detection apparatus, the reception probe is positioned with respect to the transmission probe so that it is on the acoustic axis of the ultrasonic beam (in the direction in which the intensity of the incident ultrasonic beam is a maximum) which are transmitted from the transmission probe into the object being inspected and are reflected therefrom, based on the concept of geometric optics, as shown in, for instance, column 2, line 15, to column 4, line 3, of Japanese Publication of Patent Application No. 58-26550 (1983) "Method and apparatus of ultrasonic flaw detection using two-probes".

However, in the prior art, the intensity of the received ultrasonic wave is not always a maximum at the position of the geometric-optical reflection of the acoustic axis, depending on the shape of the object 1 being inspected and the angle of incidence of the ultrasonic waves to the object. Any difference between the intensity at that position and the maximum thereof depends on the thickness of the object, and this difference increases with the thickness. Consequently, the conventional apparatus in which the reception probe is placed at the position of the geometric-optical reflection of the acoustic axis, in the ultrasonic detection of flaws in a thick-wall material, has the problem that the reception intensity decreases, and thus the sensitivity of detection of flaws drops.

SUMMARY OF THE INVENTION

An object of the present invention is to provide a two-probe ultrasonic flaw detection apparatus which enables the detection of flaws with a high degree of sensitivity.

The present invention is characterized in that the intensity at various reception positions is calculated from or experimented on the position of the transmission probe, as well as the various characteristics with respect to ultrasonic waves of the transmission and reception probes and the object being inspected, and the dimensions thereof, etc., and the reception probe is placed at the position at which the reception intensity is a maximum.

DETAILED DESCRIPTION OF THE PREFERRED EMBODIMENTS

Figure 1:
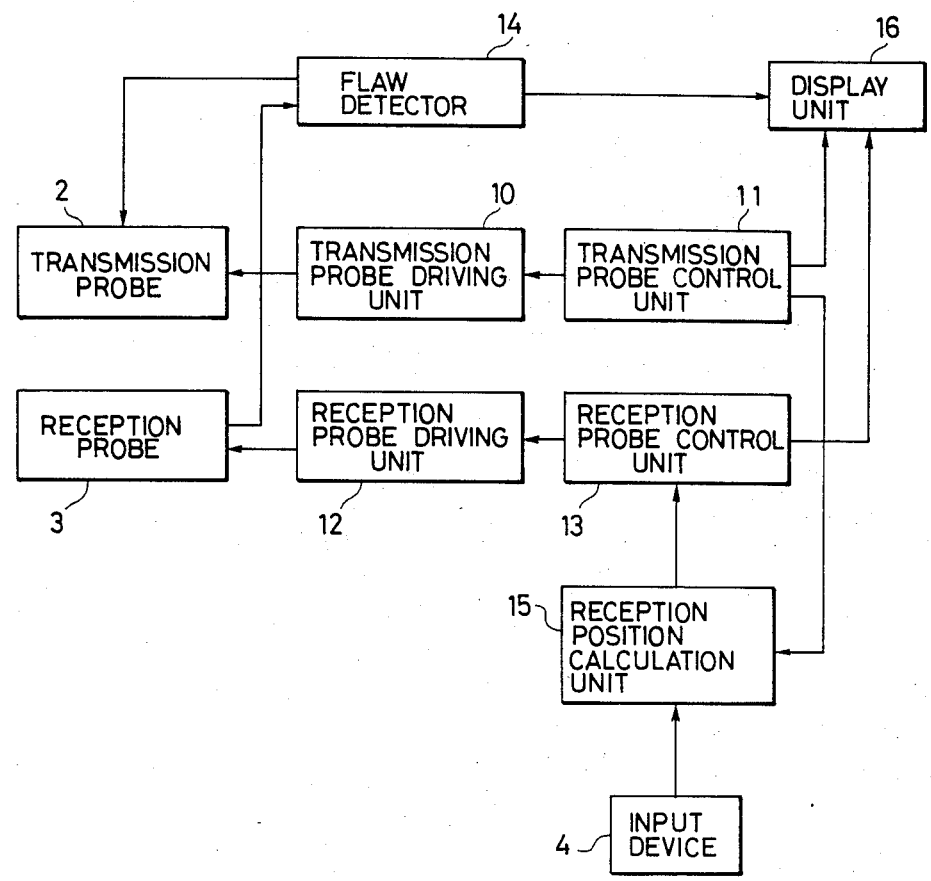
FIG. 1 is a block diagram of one embodiment of the present invention.

Referring to FIG. 1, a control unit 11 for a transmission probe generated a driving signal to a driving unit 10 for the transmission probe so that the position of the transmission probe 2 and the angle of incidence are prescribed, making it possible for the acoustic axis of incident ultrasonic waves transmitted from the transmission probe 2 into an object being inspected reach a portion which is being checked for flaws. The position of the transmission probe 2 are input to a reception position calculation unit 15 from a transmission probe control unit 11. The input device 4 is a terminal equipment used for inputting parameters concerning probes and object being inspected to the reception position calculation unit 15. The parameters concerning probes consist of dimensions of the ultrasonic transducer for transmitting ultrasonic wave therefrom, frequency of the ultrasonic wave therein, and the angle of incidence $\beta$ of the ultrasonic wave into the object being inspected. The parameters concerning object being inspected consist of the shape thereof, and the sound speed thereof, etc. When a sector scanning probe is used as a transmission probe for transmitting ultrasonic wave therefrom, the variable angle of incidence $\beta$ of ultrasonic wave into the object being inspected, is input from the transmission probe control unit 11. This unit 15 calculates the position at which the reception intensity is a maximum based on the signals from the input device 4, and the transmission probe control unit 11, in a manner which will be described later in detail, and positional information thus obtained is sent to a control unit 13 for driving the reception probe. The control unit 13 generates a driving signal to a driving unit 12 for the reception probe so that it moves the reception probe 3 to the position calculated by the reception position calculation unit 15. When the transmission and reception probes 2 and 3 are finally positioned, a flaw detector 14 outputs to the transmission probe 2 a signal making this probe transmit ultrasonic waves. The ultrasonic wave thus transmitted are received by the reception probe 3 through the object being inspected, and a signal from this probe is received and processed. An image display unit 16 displays any flaws in the object in a three-dimensional view based on the input signals from the flaw detector 14, the transmission probe control unit 11, and the reception position calculation unit 15. The position of the transmission probe 2 is then moved, and the sequence of operations described above is repeated.

Figure 2:
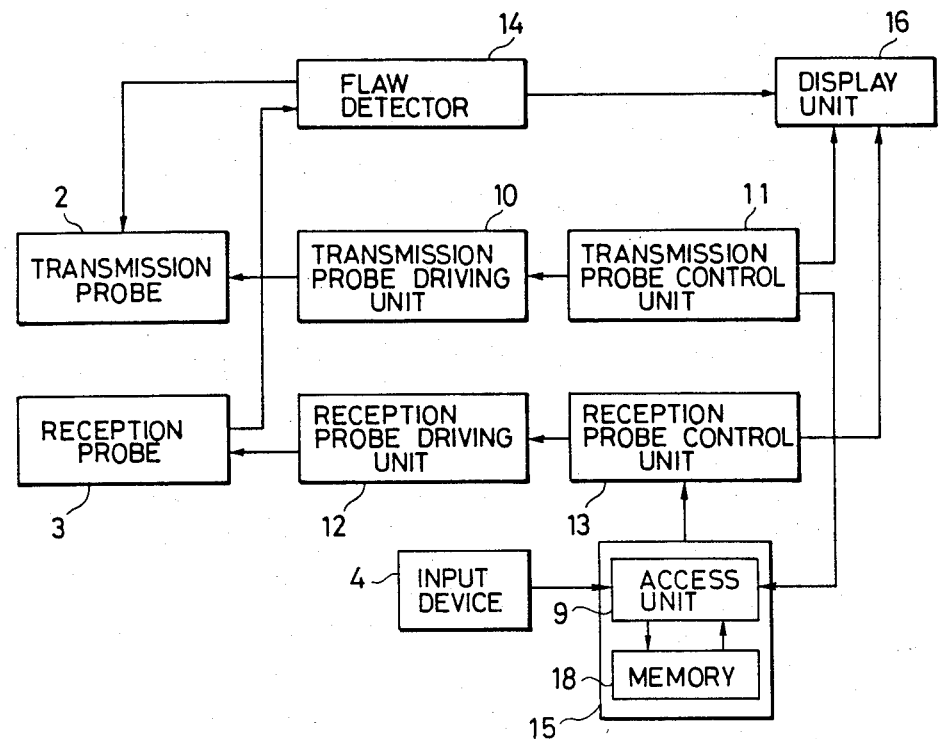
FIG. 2 is a block diagram of another embodiment of the present invention.

Referring to FIG. 2, the difference between the apparatus shown in FIG. 2 and that of FIG. 1 is as follows. In FIG. 1, the position at which the intensity of the ultrasonic wave received by the reception probe 3 is maximum, is calculated by the reception position calculation unit 15 itself. On the contrary, the apparatus shown in FIG. 2 stores the maximum reception position beforehand which was obtained by calculation or experiment mentioned later within a memory 18. When the parameters concerning probes and object being inspected and position of transmission probe, angle of incidence of ultrasonic waves to object being inspected in the case of using a sector scanning probe are input to the access unit 9 of the reception position calculation unit 15 from the input device 4 and the transmission probe control unit 11, respectively, the access unit 9 reads out the maximum reception strength position corresponding to the input signals from the input device 4 and the transmission probe control unit 11, and controls the reception probe control unit 13.

In the embodiment shown in FIG. 1, a method of determining the position at which the intensity of received ultrasonic wave is a maximum, is explained hereunder.

Figure 3:
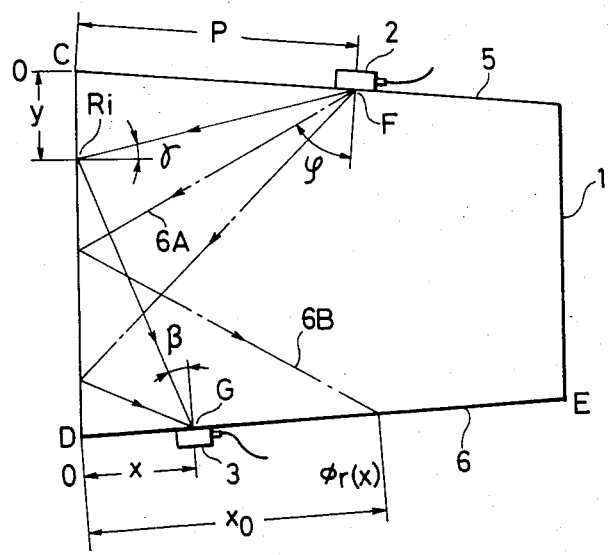
FIG. 3 is an explanation drawing how to calculate reception intensity based on the positional relationship between transmission and reception probes when the transmission and reception probes are placed on opposite surfaces of an object being inspected.

Referring to FIG. 3, the transmission and reception probes 2 and 3 are placed on the object 1 being inspected. The conventional apparatus is constructed on the assumption that the acoustic axis 6A of the ultrasonic wave transmitted from the transmission probe 2 is reflected by a reflection plane CD and is directed along acoustic axis 6B to the geometric-optical reflection position. According to the present invention, however, the position at which the intensity of received ultrasonic wave is maximum is calculated by a method described below, based on the fact that the geometric-optical position of the acoustic axis 6B is not always the same as the position at which the intensity of received ultrasonic wave is maximum. If the reception probe 3 is positioned at a distance x from a point D along a reception surface DE, ultrasonic waves reaching this probe are a combination of all waves reflected from various points of reflection plane CD. When point $R_i$ is a distance y from a point C on a reflection plane CD and the transmission probe 2 is positioned at F, the length of the line from $R_i$ to F is expressed as $l_y$. The intensity of the ultrasonic waves transmitted from the transmission probe 2 has directionality in that it is strongest in the center of the ultrasonic beam, i.e., along the acoustic axis 6A, and becomes weaker further from the sound axis. Therefore, if the intensity of the ultrasonic waves transmitted from the transmission probe 2 toward the point $R_i$ is expressed as $D_i$ (hereinafter called the directionality coefficient), it is a function of y. If the rate of attenuation due to the propagation length $l_y$ of the ultrasonic waves from point F to $R_i$ is denoted by $L_i$, this is also a function of y. The instantaneous value $\phi_i(y)$ of the ultrasonic waves reaching point $R_i$ is given by Equation (1):

$$\phi_i(y) = L_i \cdot D_i \exp(-i \cdot k \cdot l_y) \tag{1}$$

In this equation, i denotes an imaginary number $\sqrt{-1}$, and k denotes the wave number, $k = 2\pi/\lambda$ when the wave length of the ultrasonic waves is $\lambda$. $L_l$, $D_l$, and k are calculated in the reception position calculation unit 15 by the input data thereto from the input device 4. $L_l$ is decided based on the shape of the object 1 being inspected. $D_l$ is decided based on the sizes of the probes 2, 3 and frequency of the ultrasonic wave used in the probes. k is decided based on the above-mentioned frequency. The ultrasonic waves given by Equation (1) are reflected from point $R_i$, and the proportion of mode conversion from transverse waves to longitudinal waves varies with the angle of incidence $\gamma$ to the reflection plane, so that the ratio of transverse incident wave to transverse reflected wave, i.e., the reflectivity $R_s$ of ultrasonic wave, is a function of the angle of incidence $\gamma$, and this means that reflectivity is a function of the positions of the transmission probe 2 and the point $R_i$. The ultrasonic waves reflected with this reflectivity pass along a line $R_iG = l_x$, where G is the position of the reception probe 3, while being attenuated by $L_r$, and enters the reception probe 3 at an angle of incidence $\beta$. The directionality coefficient $D_r$ of the reception probe and the ratio T of ultrasonics wave passing through the contact shoe of the probe 3 from the object being inspected (the ultrasonic wave transmittivity) are determined with respect to the angle of incidence $\beta$, so that they are basically determined as function of the positions of reception probe 3 and the point $R_i$. Therefore the instantaneous value of the ultrasonic wave reflected from point $R_i$ and received reception probe 3 can be given by the following equation:

$$\phi_r(x, y) = \phi_i(y) R_s D_i L_i T \exp(-i k l_x) \tag{2}$$

For instance, reflectivity $R_s$ of ultrasonic wave and the rate T at which ultrasonic wave passes from the object being inspected to the contact shoe of the probe are given by Equation (3) and (4), respectively:

$$R_s = \frac{M - \cos^2 2\gamma}{M + \cos^2 2\gamma} \tag{3}$$

where, $$M = 4 \cdot S^2 \cdot \sqrt{q^2 - S^2} \cdot \sqrt{1 - S^2}$$

$q = C_{1S}/C_{1L}$
$S = \sin \gamma$
$C_{1S}$: sound speed of transverse waves within object being inspected
$C_{1L}$: sound speed of longitudinal waves within object being inspected The rate T, for instance, is given by as follows:

$$T = -\frac{C_{1S} \cdot C_{2L}}{C_{2S}} \cdot \frac{\cos\beta}{\cos\delta} \cdot \frac{2(b^2 - 1)}{B} \tag{4}$$

where, $B = \left[\frac{(b-1)}{2a} + 2b\right] +$ $$\frac{\rho_1}{\rho_2} \left(\frac{C_{1S}}{C_{2S}}\right)^4 \left[\frac{(b'^2 - 1)^2}{2a'} + 2b'\right]$$

$$C = \frac{C_{2L}}{\sin\delta}$$

$$a = \sqrt{(C/C_{2L})^2 - 1}$$

-continued $$a' = \sqrt{(C/C_{1L})^2 - 1} \text{ (here, } (C/C_{1L}) > 1)$$

$$a' = -i\sqrt{1 - (C/C_{1L})^2} \text{ (here, } (C/C_{1L}) < 1)$$

$$b = \sqrt{(C/C_{2S})^2 - 1}$$

$$b' = \sqrt{(C/C_{1S})^2 - 1}$$

$$\delta = \sin^{-1}\left(\frac{C_{2L}}{C_{1S}} \sin\beta\right)$$

$\delta_1$: density of the object being inspected
$\delta_2$: density of the contact shoe of probe
$C_{2S}$: sound speed of transverse waves within the contact shoe of probe
$C_{2L}$: sound speed of longitudinal waves within the contact shoe of probe Values obtained from Equation (2) by transferring the point $R_i$ along the reflection plane CD are collected. In other words, the instantaneous value $\phi_r(x)$ of the ultrasonic waves received at the position G of the reception probe 3 can be determined by varying the value y in Equation (2) within the range of $0 \leq y \leq l_0 (=CD)$ from C to D along the reflection plane, and integrating it.

$$\phi_r(x) = \int_0^{l_0} \phi_r(x, y) dy \quad (5)$$

Consequently, the reception intensity $P_r(x)$ at position G can be determined by the following equation:

$$P_r(x) = |\phi_r(x)|^2 \quad (6)$$

The results of actual calculations of this intensity and a comparison with those obtained by experiments will be given below. For this purpose, a transmission surface CF in FIG. 3 is assumed to be parallel to a reception surface DG, and a reflection plane CD to be perpendicular to the transmission and reception surfaces.

Figure 4:
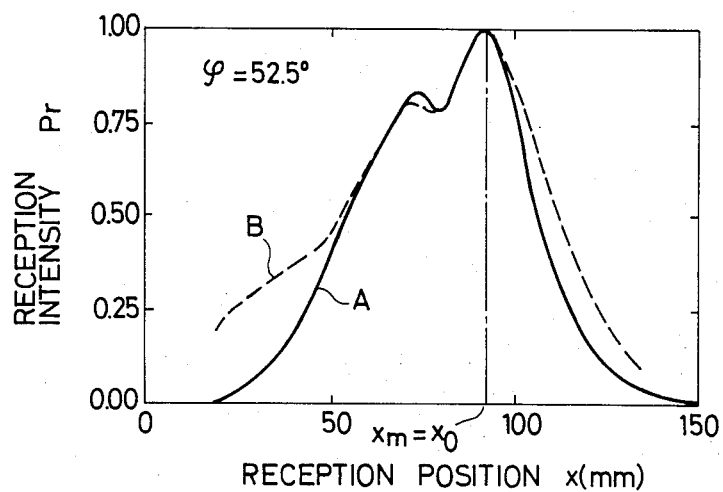
FIGS. 4 to 7 show examples of calculations for determining the positions of maximum reception intensity corresponding to the positional relationship of FIG. 3.
Figure 5:
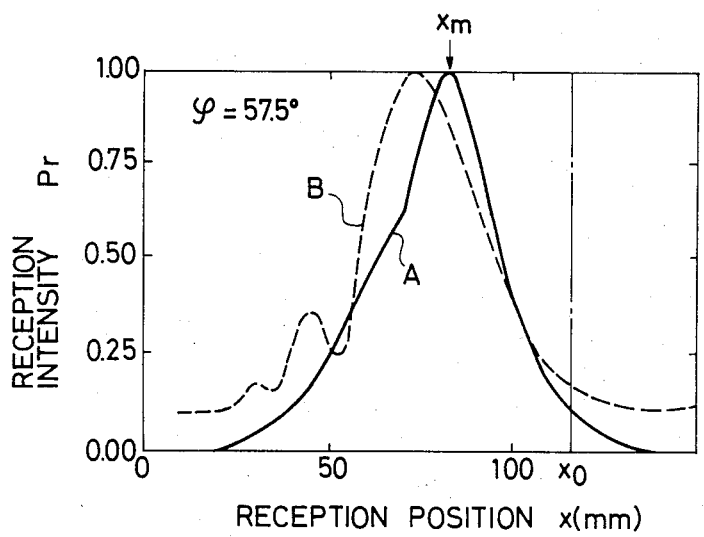
Figure 6:
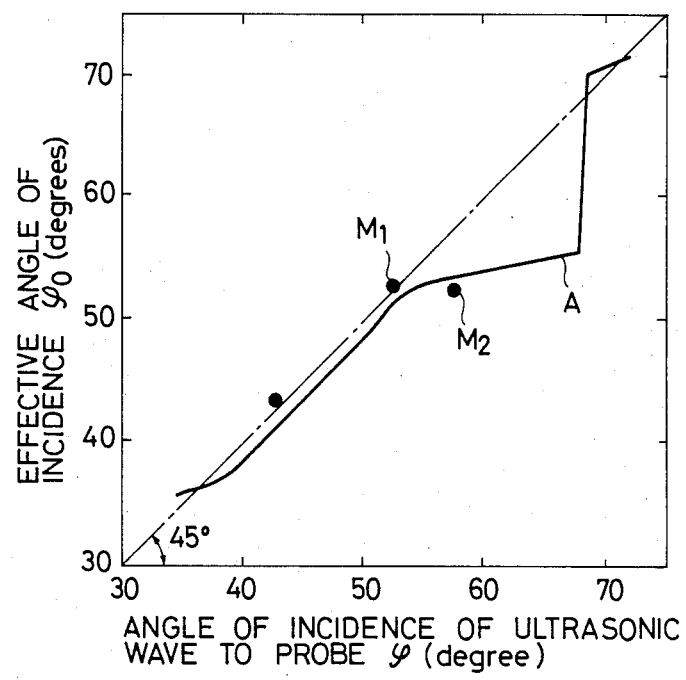

FIG. 4 is a graph of results obtained when the angle of incidence $\psi$ of the ultrasonic wave to the object being inspected was 52.5°. In this graph, the abscissa gives the reception position x and the ordinate gives the reception intensity $P_r$, the solid line A indicating calculated values and the broken line B values obtained experimentally. The position $x_m$ at which the reception intensity is a maximum both coincide with the geometric-optical reflection position $x_o$. However, when the angle of incidence $\psi$ of the ultrasonic wave to the object being inspected is 57.5°, as shown in FIG. 5, the position $x_m$ at which the calculated value A of the reception intensity is a maximum deviates to some extent (about 43 mm) from the position $x_o$ of the geometric-optical reflection position $x_o$ of the acoustic axis, although the position $x_m$ coincides in practice with that of the empirical value B. This deviation is thought to be caused mainly by the difference in ultrasonic wave reflectivity $R_s$ due to the mode conversion from transverse wave to longitudinal wave along the reflection plane. FIG. 6 shows the relationship between the angle of incidence of the ultrasonic wave into the object being inspected and the position $x_m$ at which the reception intensity is a maximum. The angle of incidence $\psi$ of the ultrasonic wave into the object being inspected is given along the abscissa, while the angle of incidence $\psi_0$ of the ultrasonic wave when the position at which the reception intensity is a maximum is regarded as the geometric-optical reflection position on the acoustic axis (hereinafter called the effective angle of incidence) is given along the ordinate. FIG. 6 shows that the position at which the reception intensity is a maximum coincides with the geometric-optical reflection position of the acoustic axis when it is located along the dot-dash line drawn at 45°. It can be seen from this graph that the position $x_m$ at which the reception intensity is a maximum is nearer to the reflection plane than the geometric-optical reflection position $x_o$ of the acoustic axis when the angle of incidence $\psi$ of the ultrasonic wave to the object being inspected is between 53° and 68°. In FIG. 6, points $M_1$ and $M_2$ indicate empirical values corresponding to the results shown in FIGS. 4 and 5, respectively.

Figure 7:
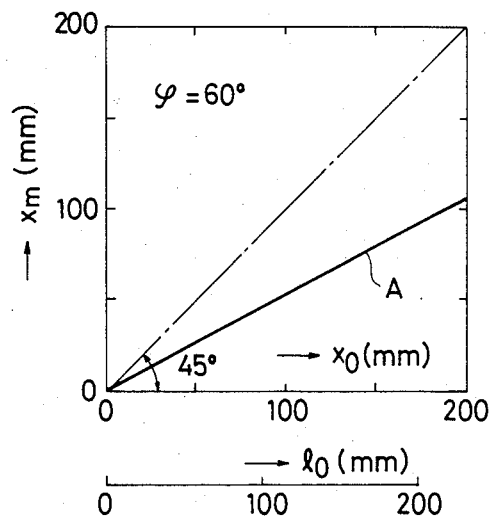

This graph illustrates how the reception intensity $P_r(x)$ varies with respect to the reception position x when the angle of incidence $\psi$ is varied under conditions in which the other parameters are fixed. FIG. 7 shows the variation of the maximum reception intensity position $x_m$ with respect to variation in the thickness $CD = l_0$ of the object 1 being inspected of FIG. 3 under conditions of a fixed angle of incidence $\psi = 60°$ at which the geometric-optical reflection position $x_o$ is not the same as the actual maximum reception intensity position $x_m$. In FIG. 7, the solid line A shows the calculated value, the geometric-optical reflection position $x_o$ is indicated, together with 0, along the abscissa, because these values are governed by the following simple relationship under conditions in which the transmission and reception surfaces are parallel to each other, a reference position x=0 is on the reflection plane, and $\psi = 60°$.

$$x_o = \sqrt{\frac{3}{2}} \, l_0 = 0.866 \, l_0$$

The position $x_m$ coincides with position $x_o$ when $x_m$ is located on dot-dash line inclined at 45°. The graph shows that this coincidence is lost when $\psi = 60°$, and that the position $x_m$ at which the reception intensity is a maximum deviates further from the geometric optical reflection point $x_o$ of the acoustic axis as $l_0$ increases.

Figure 8:
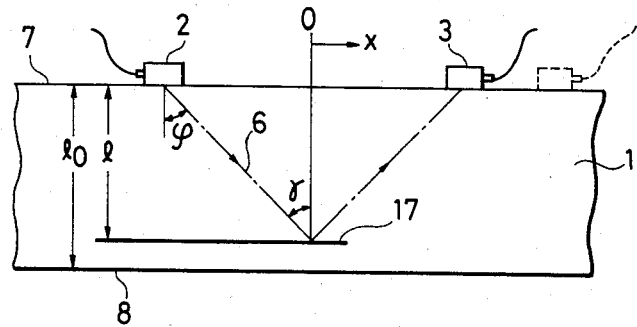
FIG. 8 is another explanation drawing showing how to calculate reception intensity based on the positional relationship between transmission and reception probes when the transmission and reception probes are placed on the same surface of an object being inspected.

The above description concerns a method of determining the position of maximum reception intensity by calculation when the transmission and reception probes 2 and 3 are placed on opposite surfaces of the object 1 being inspected, as shown in FIG. 3. However, there is another case in which the two probes 2 and 3 are placed on the same surface of the object 1, as shown in FIG. 8. In this case, the ultrasonic wave transmitted from the transmission probe 2 into the object 1 at an angle $\psi$ is reflected by a flaw 17 parallel to the transmission surface, and is received by the reception probe 3 positioned on the same surface as the transmission probe 2. The angle of incidence $\psi$ of the ultrasonic waves from the probe 2 into object 1 is equal to the angle of incidence $\gamma$ to the reflection plane in this case, whereas $\psi + \gamma = 90°$ when the transmission and reception surfaces are parallel to each other, as in FIG. 3. The angle of incidence related directly to the reception intensity is $\gamma$, so that the angle of incidence $\gamma$ to the same reflection plane as that in FIG. 3 can be obtained if the value obtained by subtracting the angle of incidence $\psi$ of FIG. 8 from 90° is taken as a new value of $\psi$. This means that FIG. 6, which shows the characteristics with respect to FIG. 3, can be regarded to show the characteristics of FIG. 8 as well if the abscissa of $\psi$ of FIG. 6 is taken to indicate values obtained by substituting $90° - \psi$ for $\psi$ in FIG. 8. For the same reason, the ordinate of FIG. 6 is taken to indicate values obtained by subtracting the effective angle of incidence from 90°. Accordingly, when $\psi = 30°$ in FIG. 8, for example, $\psi = 60°$ is read on the abscissa of FIG. 6, and the effective angle of incidence is determined to be 36°. In addition, the distance from the reference line (the line $x = 0$) to the position $x_m$ at which the reception intensity is a maximum, in this case, is larger than that to the geometric-optical reflection position of the acoustic axis. When the angle of incidence $\psi$ of the ultrasonic wave to the object being inspected is 30°, and the distance l from the transmission surface to the flaw 17 is 100 mm, for instance, the difference in distance between the position at which the reception intensity is a maximum and the position of the geometric-optical reflection of the acoustic axis is 35 mm.

Figure 9:
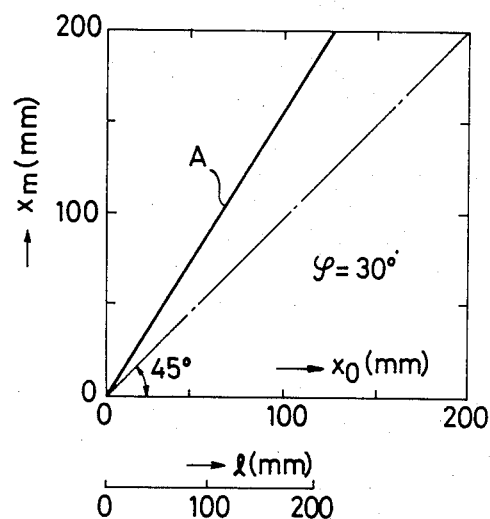
FIG. 9 shows example of calculation for determining the position of maximum reception intensity corresponding to the positional relationship of FIG. 8.

FIG. 9 shows the maximum reception intensity position $x_m$ in relation to the distance l from the transmission surface to the flaw when the angle of incidence $\psi$ of the ultrasonic waves to the object 1 being inspected in FIG. 8 is fixed at 30°. In FIG. 9, the solid line A show the calculated value. The difference between the maximum reception intensity position $x_m$ and the geometric-optical reflection position $x_o$ of the acoustic axis increases with increasing distance l from the transmission surface to the flaw.

The above description concerns cases in which the flaw is parallel or perpendicular to the transmission surface. The present invention is also applicable to the case in which the flaw is at some angle other than at right angles to the transmission surface. In this case, however, the range of the angle of incidence $\psi$ of the ultrasonic waves within which the maximum reception intensity position $x_m$ does not coincide with the geometric-optical reflection position $x_o$ of the acoustic axis differs characteristically from the range of 53° to 68° when the surface of the flaw is perpendicular to the transmission surface, or from that of 22° to 37° when it is parallel thereto.

As described above in detail with reference to FIGS. 3 to 9, the maximum reception intensity position does not always coincide with the geometric-optical reflection position of the acoustic axis. Therefore, in the example of FIG. 5 for instance, the reception intensity $P_r$ is higher by as much as about 14 $d\beta$ at the actual maximum reception intensity position $X_m$ than at the geometric-optical reflection position $x_o$. Thus, in the apparatus of the present invention, the detection sensitivity is increased by that much, and this enables the detection of flaws which have been impossible to detect heretofore. This detection can be realized by determining the maximum reception intensity position by calculations performed by the reception position calculation unit 15 of the embodiment of FIG. 1, in the following way.

Figure 10:
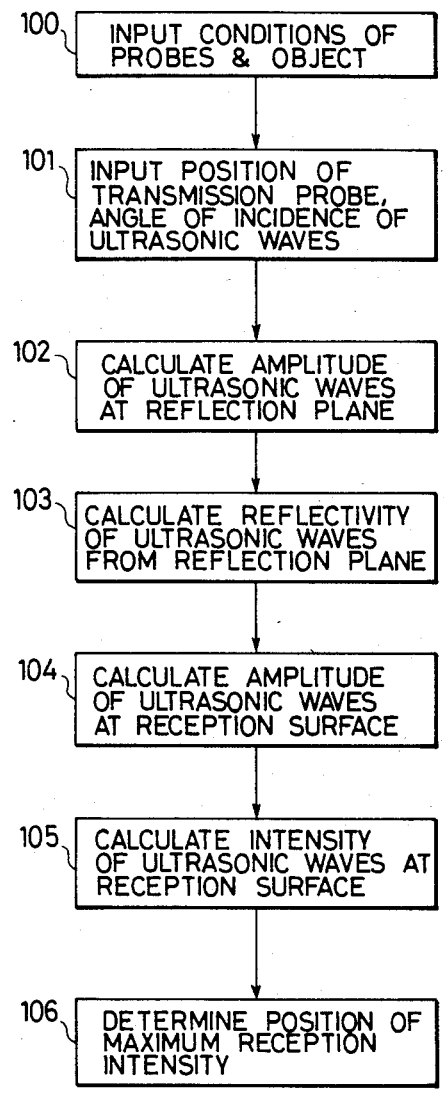
FIGS. 10 and 11 show examples of flow charts for determining the positions of maximum reception intensity corresponding to the block diagrams of FIGS. 1 and 2, respectively.

FIG. 10. shows the operation flow in the reception position calculation unit 15 shown in FIG. 1. In step 100, parameters concerning of the object being inspected, such as the sound speed of transverse ultrasonic wave in the object, and those of the probes, are input from the input device 4 to the reception position calculation unit 15. In step 101, the position of the transmission probe 2 and the angle of incidence $\psi$ of the ultrasonic waves to the object 1 being inspected in the case of using a sector scanning probe are fetched from the control unit 11 to the reception position calculation unit 15. The steps from 102 to 105 are taken place in the reception position calculation unit 15. In step 102 the amplitude $\phi_i(y)$ of the ultrasonic wave at the reflection plane is calculated using Equation (1). The reflectivity $R_s$ of the ultrasonic wave from the reflection plane is found in step 103 using Equation (3). The amplitude of the ultrasonic waves at the reception surface is determined using Equation (4) in step 104, and the intensity $P_r(x)$ of the ultrasonic waves at the reception surface is calculated using Equation (5) in step 105. These calculations are performed for various values of the position x of the reception probe 3, and the position $x_m$ at which the reception intensity is a maximum is determined therefrom, and output from the reception position calculation unit 15 to the reception probe control unit 13 in step 106. With this operation flow, the position at which the reception intensity is a maximum can be determined by calculations for any position of the transmission probe 2 and any angle of incidence of the ultrasonic wave to the object being inspected in the case of using a sector scanning probe.

Figure 11:
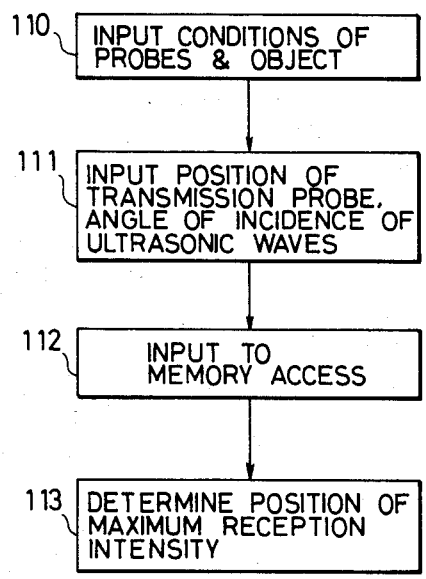

FIG. 11 shows another operation flow corresponding to FIG. 2. The position at which the reception intensity is a maximum is determined beforehand by calculations based on the position of the transmission probe 2 and the angle of incidence of the ultrasonic waves to the object being inspected in the case of using a sector scanning probe according to the steps shown in 102 to 105 of FIG. 10, or by experiment mentioned later so as to prepare a map, and this map is stored in a memory 18. In the steps 110 and 111, various parameters are fetched in the same way as in FIG. 10, and the position of the maximum reception intensity corresponding to these parameters is fetched from the memory 18 in step 112.

The maximum reception intensity position which is arranged as shown in FIGS. 3 and 8 can be obtained by experiment as follows:

(a) arranging the transmission probe 2 on the transmission plane 5, 7, on which an acoustic axis of a ultrasonic wave transmitted from the transmission probe 2 reaches to a position to be detected a flaw of the object 1 being inspected, (b) moving the reception probe 3 along the reception surface 6, 7 from the starting point ($x = 0$) of the flaw detection, and reading out the intensity of ultrasonic waves at all points on the reception surface (6, 7), and (c) getting the maximum reception intensity positions among the intensity of the ultrasonic wave corresponding to the every reception points. This operation flow shown in FIG. 11 is characterized in that the position at which the reception intensity is a maximum can be determined quicker than in the previous flow shown in FIG. 10, since no calculations are required every time the position of the transmission probe and the angle of incidence of the ultrasonic waves to the object being inspected in the case of using a sector scanning probe are changed.

As is clear from the above embodiments, the present invention has the effect that the sensitivity of detection of flaws can be increased by so much that it is possible to detect flaws which can not be detected by any conventional methods because of the low reception intensity of reflected wave therein, since the present invention makes it possible to place the reception probe at a position at which the reception intensity is a maximum.

What we claim is:

1. In a two-probe ultrasonic flaw detection apparatus in which an ultrasonic wave is transmitted from a transmission probe into an object being inspected, and ultrasonic waves reflected from a reflection surface in said object are received by a reception probe provided separately from said transmission probe; a two-probe ultrasonic flaw detection apparatus comprising:

maximum reception intensity position determination means which determines the position at which the combined intensity of ultrasonic waves reflected from each part of said reflection surface form a maximum, using as input parameters the ultrasonic characteristics of said object being inspected and of said transmission and said reception probes, and a position of said transmission probe and an angle of incidence onto said object, and reception probe position-controlling means which drives said reception probe to said position of said maximum reception intensity determined by said determination means.

2. A two-probe ultrasonic flaw detection apparatus according to claim 1, characterized in that said maximum reception intensity position determination means calculates said position of said maximum reception intensity based on following steps using said input parameters every time the values of said input parameters are renewed, (a) calculating an amplitude of an ultrasonic wave at a reflection plane, (b) calculating a reflectivity of an ultrasonic wave from a reflection plane, (c) calculating an amplitude of ultrasonic wave at a reception surface, and (d) calculating a intensity of ultrasonic waves at said reception surface.

3. A two-probe ultrasonic flaw detection apparatus according to claim 2, characterized in that said maximum reception intensity position determination means comprising a memory which stores said maximum reception intensity positions obtained by said steps, and a access means which reads out from said memory the maximum reception intensity position corresponding to the input parameters when said input parameters are given.

4. A two-probe ultrasonic flaw detection apparatus according to claim 1, characterized in that said maximum reception intensity position determination means comprising a memory which stores said maximum reception intensity positions obtained by an experiment, and a access means which reads out from said memory the maximum reception intensity position corresponding to the input parameters when said input parameters are given.

5. A two-probe ultrasonic flaw detection apparatus according to claim 4, characterized in that said maximum reception intensity position determination means stores said position of said maximum reception intensity based on following steps using said input parameters every time the values of said input parameters are renewed, (a) arranging said transmission probe on a transmission surface on which an acoustic axis of said ultrasonic wave transmitted from said transmission probe reaches to a position to be detected a flaw in an object being inspected, (b) moving said reception probe along the reception surface from a starting point of the flaw detection and reading out said intensity of ultrasonic wave in each point on said reception surface, and (c) storing said maximum reception intensity positions among said intensity of ultrasonic wave corresponding to the detected points to said memory.

6. A two-probe ultrasonic flaw detection apparatus according to claim 1, characterized in that said ultrasonic characteristics of the object being inspected and of said transmission and said reception probe are input from a input device used for a terminal equipment to said maximum reception intensity position determination means.

7. A two-probe ultrasonic flaw detection apparatus according to claim 6, characterized in that said angle of incidence is input from said input device to said maximum reception intensity position determination means.

8. A two-probe ultrasonic flaw detection apparatus according to claim 1, characterized in that said position of said transmission probe is input from a control unit for said transmission probe to said maximum reception intensity position determination means.

9. A two-probe ultrasonic flaw detection apparatus according to claim 8, characterized in that said angle of incidence is input from said control unit to said maximum reception intensity position determination means.

* * * * *